(12) United States Patent
Hansen et al.

(10) Patent No.: US 6,232,310 B1
(45) Date of Patent: May 15, 2001

(54) FUSED 1,4-THIAZINE-2-CARBONITRILE DERIVATIVES, THEIR PREPARATION AND USE

(75) Inventors: Holger Claus Hansen, Værløse; Tina Møller Tagmose, Ballerup; John Bondo Hansen, Jyderup, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/520,447

(22) Filed: Mar. 8, 2000

Related U.S. Application Data

(60) Provisional application No. 60/125,883, filed on Mar. 24, 1999.

(30) Foreign Application Priority Data

Mar. 12, 1999 (DK) ............................................ 1999 00353

(51) Int. Cl.[7] .................... C07D 279/16; A61K 31/5415; A61P 5/48
(52) U.S. Cl. ............................ 514/224.2; 544/51; 544/52
(58) Field of Search .......................... 514/224.2; 544/51, 544/52

(56) References Cited

FOREIGN PATENT DOCUMENTS

WO 97/26265    7/1997 (WO) .

OTHER PUBLICATIONS

El–Taweel et al., Arch. Pharm. Res., vol. 13, No. 3, pp. 261–264 (1990).
Liso et al., J. Heterocyclic Chem., vol. 17, pp. 793796 (1980).
Liso et al., J. Chem. Soc. Perkin Trans.I, pp. 567–572 (1983).
Liso et al., Communications, Synthesis, pp. 755–757 (Sep. 1983).
Kano et al., Heterocycles, vol. 12, No. 5 (1979).
Liso et al., J. Heterocyclic Chem., vol. 18 No. 279 (1981).
Stephens et al., J. Heterocyclic Chem., vol. 34, pp. 857–860 (1997).
Stephens et al., J. Heterocyclic Chem., vol. 35, pp. 927–931 (1998).
Wang et al., Pakistan J. Sci. Ind., Res., pp. 242–244, vol. 31, No. 4, (Apr. 1988).
Baliah et al., Indian Journal of Chemistry, vol. 10, pp. 917–918 (Sep. 1972).
Pirotte et al., Biochemical Pharmacology, vol. 47, pp. 1381–1386 (1994).
Pirotte et al., J. Med. Chem., vol. 36, pp. 3211–3213 (1993).
Vlahos et al., Metabolism, vol. 40, pp. 825–829 (1991).
Alemzadeh et al., Journal of Clinical Endocrinology and Metabolism, vol. 83, pp. 1911–1915 (1998).
Cobb, Jeff and Dukes, Iain in Annual Reports in Medicinal Chemistry, vol. 33, James Bristol, ed., Academic Press, San Diego, 1998, p 213–222.*
Kano, Shinzo; Yuasa, Yoko; Ono, Toshihiro; Shibuya, Shiroshi, Heterocycles (1979), 12(5),681–4.*

* cited by examiner

Primary Examiner—Mukund J. Shah
Assistant Examiner—Thomas McKenzie
(74) Attorney, Agent, or Firm—Steve T. Zelson, Esq.; Carol E. Rozek, Esq.

(57) ABSTRACT

The present invention relates to fused 1,4-thiazine-2-carbonitrile derivatives, compositions thereof and methods for preparing the compounds.

The compounds are useful in the treatment of diseases of the central nervous system, the cardiovascular system, the pulmonary system, the gastrointestinal system and the endocrinological system.

18 Claims, No Drawings

FUSED 1,4-THIAZINE-2-CARBONITRILE DERIVATIVES, THEIR PREPARATION AND USE

CROSS-REFERENCE TO RELATED APPLICATIONS

This application claims priority under 35 U.S.C. 119 of Danish application PA 1999 00353 filed Mar. 12, 1999, and of U.S. Provisional application 60/125,883 filed Mar. 24, 1999, the contents of which are fully incorporated herein by reference.

FIELD OF THE INVENTION

The present invention relates to fused 1,4-thiazine-2-carbonitrile derivatives, to methods for their preparation, to compositions comprising the compounds, to the use of these compounds as medicaments and their use in therapy e.g. in the treatment or prevention of diseases of the central nervous system, the cardiovascular system, the pulmonary system, the gastrointestinal system and the endocrinological system.

Optionally, the pharmaceutical composition of the invention may comprise a compound of formula I combined with one or more other pharmacologically active compounds, e.g. an antidiabetic or other pharmacologically active material, including compounds for the treatment and/or prophylaxis of diabetes, including prevention or slowing of progression of impaired fasting glucose (IFG) and impaired glucose tolerance (IGT), as well as insulin resistance and diseases wherein insulin resistance is the pathophysiological mechanism. Suitable antidiabetics comprise short and long acting insulins, insulin analogues as well as orally active hypoglycaemic agents such as sulphonylureas, e.g. glibenclamide and glipizide; biguanides, e.g. metformin; benzoic acid derivatives, e.g. repaglinide; thiazolidin-ediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

BACKGROUND OF THE INVENTION

Potassium channels play an important role in the physiological and pharmacological control of cellular membrane potential. Amongst the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas, which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hairgrowth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labour.

By acting on potassium channels of the central nervous system these compounds can be used for treatment of various neurological and psychiatric diseases such as Alzheimer, epilepsia and cerebral ischemia.

Further, the compounds are found to be useful in the treatment of benign prostatic hyperplasia, erectile dysfunction and in contraception.

Compounds of the present invention, which inhibit insulin secretion by activating potassium channels of the beta-cell can be used in combination with other compounds which may be used to treat non-insulin dependent diabetes mellitus and insulin dependent diabetes mellitus. mellitus including prevention or slowing of progression of impaired fasting glucose (IFG) and impaired glucose tolerance (IGT). Examples of such compounds are short and long acting insulins, insulin analogues, insulin sentizers, insulin secretagogues as well as orally active hypoglycaemic agents such as sulphonylureas, e.g. glibenclamide and glipizide; biguanides, e.g. metformin; benzoic acid derivatives, e.g. repaglinide; thiazolidinediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

Since some $K_{ATP}$-openers are able to antagonize vasospasms in basilar or cerebral arteries the compounds of the present invention can be used for the treatment of vasospastic disorders such as subarachnoid haemorrhage and migraine.

Potassium channel openers hyperpolarize neurons and inhibit neurotransmitter release and it is expected that the present compounds can be used for the treatment of various diseases of the central nervous system, e.g. epilepsia, ischemia and neurodegenerative diseases, and for the management of pain.

Recently, it has been shown that diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol*, 47, 1381–1386 (1994); Pirotte B. et al., *J. Med. Chem.*, 36, 3211–3213 (1993); PCT Publication No. WO 97/26265. Diazoxide has furthermore been shown to delay the onset of diabetes in BB-rats ( Vlahos WD et al. *Metabolism* 40, 39–46 (1991)). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that compounds which activate $K_{ATP}$-channels can be used for treatment of diseases characterised by an overproduction of insulin and for the treatment and prevention of diabetes.

Certain 1,2,4-benzothiadiazine 1,1-dioxides have been proposed to act as potential α1-adrenoceptor antagonists (Chern, J.-W. et al, *J. Med. Chem.* (1998), 41, 3128–41).

3-(Alkylamino)-4H-pyrido[4,3-e]-1,2,4-benzothiadiazine 1,1-dioxides have been described recently (Neill, C. G. et al, *Tetrahedron* (1998), 54, 13645–13654) and Pirotte, B et al, *J. Med. Chem.* (1998), 41, 2946–2959).

International PCT Publication No. WO 97/26265 discloses a class of fused 1,2,4-thiadiazine and fused 1,4-thiazine derivatives being useful in the treatment of various diseases acting as potassium channel openers.

1,4-Benzothiazin-2-carbonitriles (El-Taweel et al., *Arch. Pharmacol. Res.*, 13, 261–264 (1990), Liso et al., *Synthesis*, 1983, 755–757, Liso et al., *J. Chem. Soc. Perkin I*, 1983, 567–572, Liso et al., *J. Heterocycl. Chem.*, 17, 793 (1980), Kano et al., *Heterocycles*, 12, 681–684 (1979) and Liso et al., *J. Heterocycl. Chem.*, 18, 279 (1981)), furo[3,2-b]-1,4-carbonitrile 1,1-dioxides (Stephens and Sowell, *.Heterocycl. Chem.* 34, 857–860 (1997)), thieno[3,2-b]-1,4-thiazine 1,1-dioxides (Sthephens and Sowell, *J. Heterocycl. Chem.* 35, 927–931 (1998)), pyrrolo[3,2-b]-1,4-thiazine 1,1-dioxides (Wang, Bayomi and Sowell, Pakistan J. Sci. Ind. Res. 31, 242–244 (1988)) and 2,3-dihydro-1,4-benzothiazin-2-carbonitrile 1,1-dioxides (V. Baliah and S. Ananthapadmanabhan, *Indian J. Chem.*, 10, 917–918 (1972)) have been described, but not as acting as potassium channel openers.

DESCRIPTION OF THE INVENTION

The present invention relates to fused 1,4-thiazine-2-carbonitrile derivatives of the general formula (I)

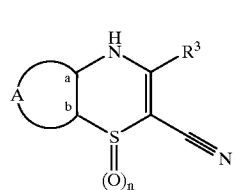

(I)

wherein
n is 1 or 2;
$R^3$ is hydrogen; $C_{1-6}$-alkyl, $C_{2-6}$-alkenyl, $C_{2-6}$-alkynyl, $C_{3-6}$-cycloalkyl or $C_{3-6}$-cycloalkyl-$C_{1-6}$-alkyl optionally being mono- or polysubstituted with hydroxy or halogen; aryl, aryl-$C_{1-6}$-alkyl, heteroaryl or heteroaryl-$C_{1-6}$-alkyl, aryl or heteroaryl optionally being mono- or polysubstituted with halogen, hydroxy, trifluoromethyl, $C_{1-6}$-alkyl or $C_{1-6}$-alkoxy;
A together with the carbon atoms a and b of formula (I) forms a ring selected from

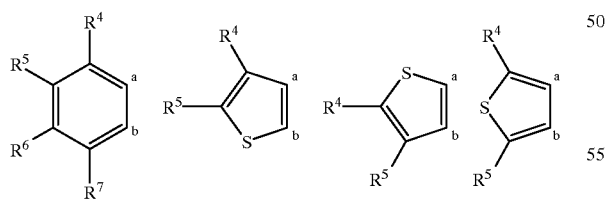

wherein $R^4$, $R^5$, $R^6$, $R^7$ independently are hydrogen; halogen; hydroxy; cyano; trifluoro-methyl; trifluoromethylsulfanyl; trifluoromethoxy; $C_{1-6}$-alkyl; $C_{1-6}$-alkoxy; $C_{1-6}$-alkoxy-$C_{1-6}$-alkyl; $C_{1-6}$-alkylsulfanyl; $C_{1-6}$-alkylsulfonyl; $C_{1-6}$-alkylsulfinyl; aryl, arylsulfanyl, arylsulfinyl, arylsulfonyl, aryloxy, the aryl group optionally being mono- or polysubstituted with halogen, hydroxy, trifluoromethyl, $C_{1-6}$-alkyl or $C_{1-6}$-alkoxy;

or a salt thereof with a pharmaceutically acceptable acid or base, or any optical isomer or mixture of optical isomers, including a racemic mixture, or any tautomeric form.

Further, the present invention relates to compounds of the general formula (I) wherein A together with the carbon atoms a and b is

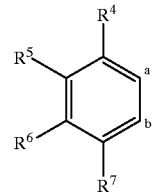

Further, the present invention relates to compounds of the general formula (I) wherein $R^3$ is $C_{1-6}$-alkyl.

Further, the present invention relates to compounds of the general formula (I) wherein wherein $R^4$, $R^5$, $R^6$, $R^7$ independently are hydrogen; halogen or trifluoromethyl.

Further, the present invention relates to compounds of the general formula (I) wherein $R^5$ and $R^6$ independently are trifluoromethyl or halogen and the remaining substituents are hydrogen.

Furthermore, the present invention claims fused 1,4-thiazine-2-carbonitrile derivatives of the general formula (I)

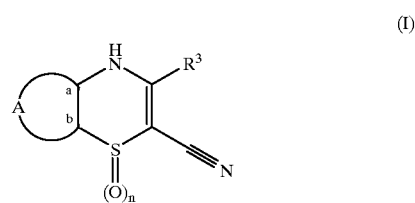

(I)

wherein
n is 1 or 2;
$R^3$ is $C_{1-6}$-alkyl, $C_{2-6}$-alkenyl, $C_{2-6}$-alkynyl, $C_{3-6}$-cycloalkyl, $C_{3-6}$-cycloalkyl-$C_{1-6}$-alkyl or $C_{1-6}$-alkyl-$C_{3-6}$-cycloalkyl, optionally being mono- or polysubstituted with hydroxy or halogen; aryl, aryl-$C_{1-6}$-alkyl, heteroaryl or heteroaryl-$C_{1-6}$-alkyl, aryl or heteroaryl optionally being mono- or polysubstituted with halogen, hydroxy, trifluoromethyl, $C_{1-6}$-alkyl or $C_{1-6}$-alkoxy;
A together with the carbon atoms a and b of formula (I) is

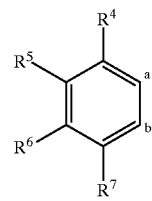

wherein $R^4$, $R^5$, $R^6$, $R^7$ independently are hydrogen; halogen; hydroxy; cyano; trifluoro-methyl; trifluoromethylsulfanyl; trifluoromethoxy; $C_{1-6}$-alkyl; $C_{1-6}$-alkoxy; $C_{1-6}$-alkoxy-$C_{1-6}$-alkyl; $C_{1-6}$-alkylsulfanyl; $C_{1-6}$-alkylsulfonyl; $C_{1-6}$-alkylsulfinyl; aryl;

or a salt thereof with a pharmaceutically acceptable acid or base.

Within its scope the invention includes all optical isomers of compounds of formula I, some of which are optically active, and also their mixtures including racemic mixture thereof.

The scope of the invention also includes all tautomeric forms of the compounds of formula I as well as metabolites or prodrugs.

A "metabolite" of a compound disclosed in this application is an active derivative of a compound disclosed herein which is produced when the compound is metabolized. Metabolites of compounds disclosed herein can be identified either by administration of a compound to a host and an analysis of blood samples from the host, or by incubation of compounds with hepatic cells in vitro and analysis of the incubant. A "prodrug" is a compound that either is converted into a compound disclosed in the application in vivo or has the same active metabolite as a compound disclosed in this application.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "halogen" means fluorine, chlorine, bromine or iodine.

The terms "$C_{1-6}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkoxy-$C_{1-6}$-alkyl" as used herein refers to a group of 2–12 carbon atoms interrupted by an O such as e.g. $CH_2$—O—$CH_3$, $CH_2$—O—$CH_2$—$CH_3$, $CH_2$—O—$CH(CH_3)_2$ and the like.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "$C_{2-6}$-alkynyl" as used herein refers to unsaturated hydrocarbons which contain triple bonds, such as e.g. —C≡—CH, —C≡CCH$_3$, —CH$_2$C≡CH, —CH$_2$CH$_2$C≡CH, —CH(CH$_3$)C≡CH, and the like.

The term "$C_{3-6}$-cycloalkyl" as used herein refers to a radical of a saturated cyclic hydrocarbon with the indicated number of carbons such as cyclopropyl, cyclobutyl, cyclopentyl, or cyclohexyl.

The term "($C_{3-6}$-cycloalkyl)-$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "$C_{1-6}$-alkylsulfanyl" as used herein, alone or in combination, refers to a straight or branched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "aryl" as used herein refers to phenyl, 1-naphthyl, or 2-naphthyl.

The term "aryl-$C_{1-6}$-alkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylsulfanyl" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pyridine, and purine.

The term "heteroaryl-$C_{1-6}$-alkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

In one embodiment of the invention n is 2.

In another embodiment of the invention $R^3$ is $C_{1-6}$-alkyl, preferably methyl.

In another embodiment of the invention $R^4$, $R^5$, $R^6$, $R^7$ are independently hydrogen, halogen, trifluoromethyl, trifluoromethoxy or trifluoromethylsulfanyl.

In another embodiment of the invention $R^4$ is hydrogen and $R^5$, $R^6$, $R^7$ are independently hydrogen, halogen, trifluoromethyl, trifluoromethoxy or trifluoromethylsulfanyl.

In another embodiment of the invention $R^5$ and $R^6$ are independently trifluoromethyl or halogen, and $R^4$ and $R^7$ are hydrogen.

In another embodiment of the invention $R^4$, $R^6$ and $R^7$ are hydrogen, and $R^5$ is halogen, trifluoromethyl, trifluoromethoxy or trifluoromethylsulfanyl.

In another embodiment of the invention $R^4$, $R^5$ and $R^7$ are hydrogen, and $R^6$ is halogen, trifluoromethyl, trifluoromethoxy or trifluoromethylsulfanyl.

Specific compounds of the invention are:

3,7-Dimethyl-4H-thieno[3,2-b]-1,4-thiazine-2-carbonitrile 1,1-dioxide;

3-Phenyl-4H-1,4-benzothiazine-2-carbonitrile 1,1-dioxide;

3-Phenyl-4H-1,4-benzothiazine-2-carbonitrile 1-oxide;

7-Chloro-3-methyl-4H-1,4-benzothiazine-2-carbonitrile 1,1-dioxide;

3-Methyl-6-trifluoromethyl-4H-1,4-benzothiazine-2-carbonitrile 1,1-dioxide;

3-Methyl-6-trifluoromethyl-4H-1,4-benzothiazine-2-carbonitrile 1,1-oxide;

7-Chloro-3-propyl-4H-1,4-benzothiazine-2-carbonitrile 1,1-dioxide;

7-Chloro-3-isopropyl-4H-1,4-benzothiazine-2-carbonitrile 1,1-dioxide;

3-tert-Butyl-7-chloro-4H-1,4-benzothiazine-2-carbonitrile 1,1-dioxide;

7-Methoxy-3-methyl-4H-1,4-benzothiazine-2-carbonitrile 1,1-dioxide;

7-Methoxy-3-propyl-4H-1,4-benzothiazine-2-carbonitrile 1,1-dioxide;

7-Methoxy-3-isopropyl-4H-1,4-benzothiazine-2-carbonitrile 1,1-dioxide;

3-tert-Butyl-7-methoxy-4H-1,4-benzothiazine-2-carbonitrile 1,1-dioxide;

6,7-Dichloro-3-methyl-4H-1,4-benzothiazine-2-carbonitrile 1,1-dioxide;

6-Fluoro-3-methyl-4H-1,4-benzothiazine-2-carbonitrile 1,1-dioxide;

6-Chloro-3-methyl-4H-1,4-benzothiazine-2-carbonitrile 1,1-dioxide;

8-Fluoro-3-methyl-6-trifluoromethyl-4H-1,4-benzothiazine-2-carbonitrile 1,1-dioxide;

6-Chloro-3-methyl-4H-thieno[2,3-b]-1,4-thiazine-2-carbonitrile 1,1-dioxide;

or a salt thereof with a pharmaceutically acceptable acid or base.

Other specific compounds of the invention are:

3-Propyl-6-trifluoromethyl-4H-1,4-benzothiazine-2-carbonitrile 1,1-dioxide;

5,7-Difluoro-3-methyl-4H-1,4-benzothiazine-2-carbonitrile 1,1-dioxide;

7-Fluoro-3-methyl-4H-1,4-benzothiazine-2-carbonitrile 1,1-dioxide;

6-Chloro-7-fluoro-3-methyl-4H-1,4-benzothiazine-2-carbonitrile 1,1-dioxide;

3-Methyl-7-trifluoromethylsulfanyl-4H-1,4-benzothiazine-2-carbonitrile 1,1-dioxide;

3-Methyl-7-trifluoromethoxy-4H-1,4-benzothiazine-2-carbonitrile 1,1-dioxide;

6,7,8-Trichloro-3-methyl-4H-1,4-benzothiazine-2-carbonitrile 1,1-dioxide;

or a salt thereof with a pharmaceutically acceptable acid or base.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

ATP sensitive potassium channels have been identified on mitochondrial membranes, and studies have indicated that potassium channel openers acting on such channels could play a role as cardioprotective agents (Garlid, K. D. et al, *Circulation Research* (1997), 81, 1072–1082 and Liu, Y. et al, *Circulation* (1998), 97, 2463–2469). Furthermore, compounds which depolarise mitochondrial membrane by opening of $K_{ATP}$-channels could influence mitochondrial energy metabolism and consequently effect stimulus-secretion coupling of pancreatic beta-cells (Grimmsmann T. and Rustenbeck, I, Br. *J. Pharmacol.* (1998), 123, 781–788) but also by acting as uncouplers reduce weight. Finally, compounds which effect the membrane potential of mitochondria by acting on ATP sensitive potassium channels could also modulate apoptotic and necrotic cell death (Green D. R. and Reed J. C., *Science* (1998), 281, 1309–1312). $K_{ATP}$-channel openers therefore could be important for treatment of various diseases characterised by cellular degeneration and death, e.g. Type 1 diabetes, Alzheimers disease, Parkinsons disease and stroke.

Since some $K_{ATP}$-openers are able to antagonize vasospasms in basilar or cerebral arteries the compounds of the present invention can be used for the treatment of vasospastic disorders such as subarachnoid haemorrhage and migraine.

The compounds of the present invention may also be used for the treatment of diseases associated with decreased skeletal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the urethra.

The present compounds could also be used for treatment of conditions associated with disturbances in gastrointestinal mobility such as irritable bowel syndrome. Additionally these compounds can be used for the treatment of premature labour and dysmenorrhea.

Potassium channel openers hyperpolarize neurons and inhibit neurotransmitter release and it is expected that such compounds can be used for the treatment of various diseases of the central nervous system, e.g. epilepsia, ischemia and neurodegenerative diseases, and for the management of pain.

Further, potassium channel openers promote hairgrowth, therefore, the compounds of the present invention can be used for the treatment of baldness.

Potassium channel openers also relax urinary bladder smooth muscle, thus, the compounds of the present invention can be used for the treatment of urinary incontinence.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of non-insulin dependent diabetes (NIDDM). Potassium channel openers, and hence the compounds of the present invention, can be used for counteracting reducing the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretion. Thus, the compounds of the present invention can be used for the treatment of NIDDM.

In early cases of insulin dependent diabetes (IDDM) or in prediabetic cases, potassium channel openers and hence the present compounds can be used to induce pancreatic beta-cell rest which may prevent the progression of the autoimmune disease.

The potassium channel openers of the present invention can be administered in combination with an immunosuppressant or with an agent like nicotinamide, which will reduce autoimmune degeneration of beta-cells.

Combining beta-cell rest with a treatment protecting the beta-cells against cytokine mediated beta-cell impairment-cytotoxicity is another aspect of this invention. Insulin requiring or Type 1 diabetes (IDDM) as well as late onset IDDM (also known as type 1.5. e.g. non-insulin-requiring Type 2 (NIDDM) patients with autoreactivity against beta-cell epitopes that later turns insulin requiring) have circulating autoreactive mono- cytes/lymphocytes that homes to the islets/beta-cells and releases their cytokines. Some of these cytokines (e.g. interleukin-1b (IL-1b), tumour necrosis factor a (TNFa) and interferon g (IFNg)) are specifically toxic to the beta-cells, e.g. through the induction of nitric oxide (NO) and other free radicals. Inhibition of this cytotoxicity, e.g. by co-administering nicotinamide (NA), a derivative hereof or other cytokine protective compounds to the prediabetic/diabetic patients treated with the PCO compound is an example of this aspect. Nicotinamide belongs to the B-vitamin family and is derived from nicotinic acid by amidation of the carboxyl group. It processes none of nicotine's pharmacological properties. NA is converted into NAD+, which acts as a coenzyme for proteins involved in tissue respiration. NA has been proposed to influence several of the putative intracellular molecular events following immune attack on the beta-cells. Animal experiments and early non-blinded experiments in humans have indicated a protective role of this compound against IDDM as well as in cytokine/immune mediated beta-cell destruction.

Yet another aspect of this application concerns the use of a PCO compound alone or in combination with the inhibitor of cytokine/immune mediated beta-cell impairment, in transplantation, e.g. islet transplantation into diabetes patients. The use of one or both of these treatments may reduce the risk of rejection of the transplanted islets/betacells/engineered beta-cells/pancreas.

Hyperinsulinemia and insulin resistance is associated with polycystic ovary syndrome in women. A $K_{ATP}$-channel opener, which reduce insulin secretion could be used to alleviate the symptoms of this disease (Nestler J. E. et al, *J. Clin. Endocrinol. And Metabolism.* (1989), 68, 1027–1032).

Compounds of the present invention which act as blockers of $K_{ATP}$-channels can be used for the treatment of NIDDM.

The compounds of the present invention may be used for treatment or prevention of diseases of the endocrinological system such as hyperinsulinaemia and diabetes, including prevention or slowing of progression of impaired fasting glucose (IFG) and impaired glucose tolerance (IGT).

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinaemia and treatment or prevention of diabetes, NIDDM and prevention or slowing of progression of impaired fasting glucose (IFG) and impaired glucose tolerance (IGT).

Further, the invention also relates to the use of the inventive compounds of formula I as medicaments useful for treating hyperinsulinaemia and treating or preventing diabetes, NIDDM and prevention or slowing of progression of impaired fasting glucose (IFG) and impaired glucose tolerance (IGT).

Furthermore, the pharmaceutical composition of the invention may comprise a compound of formula I combined with one or more other pharmacologically active compounds, e.g. an antidiabetic or other pharmacologically active material. Suitable antidiabetics comprise short and long acting insulins, insulin analogues as well as orally active hypoglycaemic agents such as sulphonylureas, e.g. glibenclamide and glipizide; biguanides, e.g. mefformin; benzoic acid derivatives, e.g. repaglinide; thiazolidinediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

In yet another aspect, the present invention relates to methods of preparing the above mentioned compounds. The methods comprises:

a) treating a compound of formula (II):

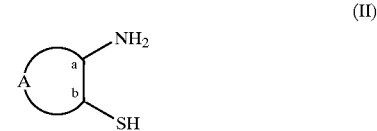

(II)

wherein A is as defined above with haloacetonitrile, e.g. iodoacetonitrile, in the presence of a base to give a compound of formula (III):

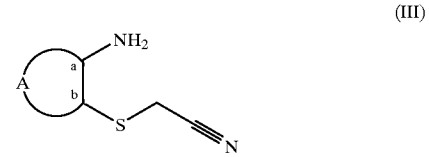

(III)

wherein A is as defined above, which by acylation with a carboxylic acid anhydride of formula $R^3$—C(=O)—O—C(=O)—$R^3$, or with an acid chloride of formula $R^3$—C(=O)Cl in the presence of a base gives a compound of formula (IV):

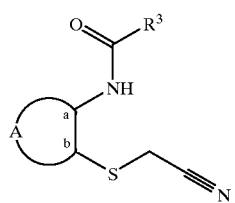

(IV)

wherein A and R³ are as defined above, which in turn by oxidation with a suitable oxidizing agent, e.g. an organic or inorganic peracid or a peroxide, selectively gives either a mono- or a dioxide of formula (V):

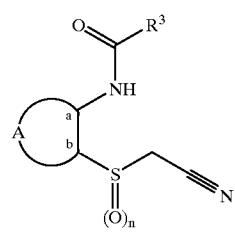

(V)

wherein A, R³ and n are as defined above.

b) treating a compound of formula (V):

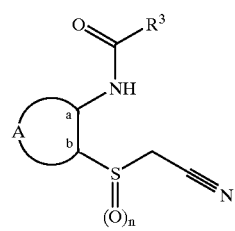

(V)

wherein A, R³ and n are as defined above with a base, e.g. a diluted aqueous solution of a metal hydroxide, gives a compound of formula (I):

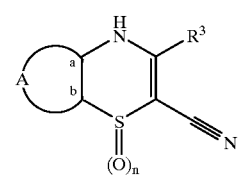

(I)

wherein A, R³ and n are as defined above.

c) acylating a compound of formula (VI):

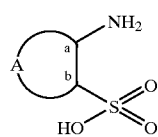

(VI)

wherein A is as defined above, with a carboxylic acid anhydride of formula R³—C(=O)—O—C(=O)—R³, or with an acid chloride of formula R³—C(=O)Cl in the presence of a base to give a compound of formula (VII):

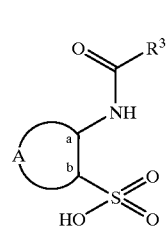

(VII)

wherein A and R³ are as defined above, which by treatment with a chlorinating agent, e.g. PCl₅, gives a compound of formula (VIII):

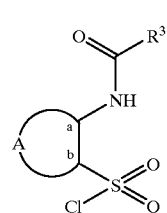

(VIII)

wherein A and R³ are as defined above, which by reduction under standard conditions gives a sulfinic acid of formula (IX):

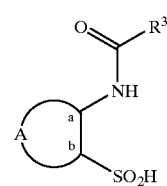

(IX)

wherein A and R³ are as defined above, which by treatment with haloacetonitrile, e.g. iodoacetonitrile, in the presence of a base gives a compound of formula (V):

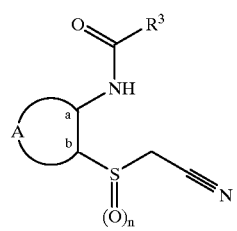

(V)

wherein A and R³ are as defined above and n is 2.

d) treating a compound of formula (X):

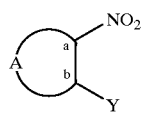

wherein A is as fined above and Y is a leaving group, preferentially halogen, with a source of HS⁻ or a HS⁻ synthon, e.g. sodium sulfide, hydrogensulfide, thiophosphate, thiosulfate, ethylthiolate, or thiourea, to give a compound of formula (XI):

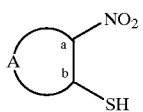

wherein A is as defined above, and subsequently alkylating (XI) with haloacetonitrile, e.g. iodoacetonitrile, in the presence of a base gives a compound of formula (XII):

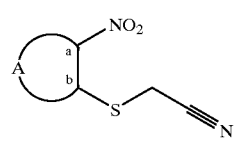

wherein A is as defined above, which by oxidation with a suitable oxidizing agent, e.g. an organic or inorganic peracid or a peroxide, selectively gives either a mono- or a dioxide of formula (XIII):

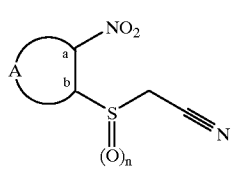

wherein A and n are as defined above, which by catalytic hydrogenation in the presence of a carboxylic acid anhydride of formula $R^3$—C(=O)—O—C(=O)—$R^3$ gives a compound of formula (V):

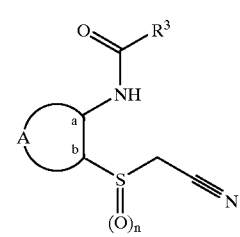

wherein A, $R^3$ and n are as defined above.

e) nitrating a compound of formula (XIV):

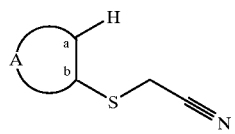

wherein A is as defined above by conventional methods to give a compound of formula (XII):

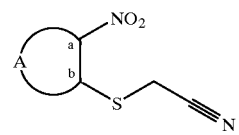

wherein A is as defined above.

f) treating a compound of formula (XV):

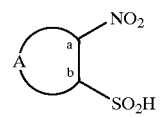

wherein A is as defined above with haloacetonitrile, e.g. iodoacetonitrile, in the presence of a base to give a compound of formula (XIII):

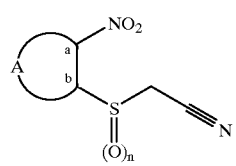

wherein A and n are as defined above.

g) oxidizing a compound of formula (XVI):

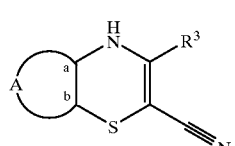

wherein A and $R^3$ are as defined above with a suitable oxidizing agent, e.g. an organic or inorganic peracid or a peroxide, to give selectively either a mono- or a dioxide of formula (I):

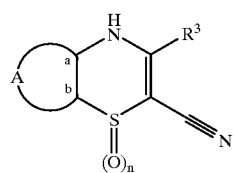

(I)

wherein A, R³ and n are as defined above.

h) oxidizing a compound of formula (III):

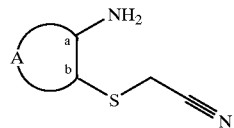

(III)

wherein A is Defined above with a suitable oxidizing agent, e.g. an organic or inorganic peracid or a peroxide, to give selectively either a mono- or a dioxide of formula (XVII):

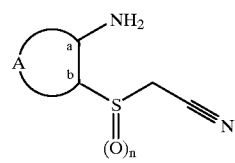

(XVII)

wherein A and n are as defined above which by acylation with a carboxylic acid anhydride of formula R³—C(=O)—O—C(=O)—R³, or with an acid chloride of formula R³—C(=O)Cl in the presence of a base gives a compound of formula (V):

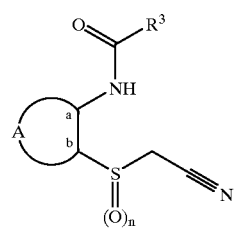

(V)

wherein A, R³ and n are as defined above.

i) treating a compound of formula (XVII):

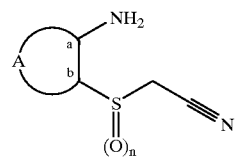

(XVII)

wherein A and n are as defined above with an orthoester R³—C(OR)₃, wherein R is methyl or ethyl, and subsequently with an organic base, e.g. a tertiary amine, to give a compound of formula (I):

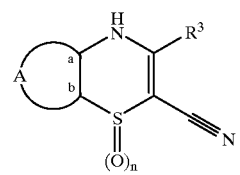

(I)

wherein A, R³ and n are as defined above.

j) treating a compound of formula (XVIII) or a dimer thereof:

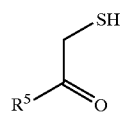

(XVIII)

wherein R⁵ is as defined above with N≡C—CH₂—SO₂—CH₂—C≡N in the presence of a base in a suitable solvent, e.g. an alcohol, to give a compound of formula (XVIII):

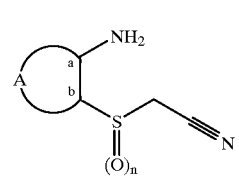

(XVII)

wherein n is 2, R⁵ is as defined above and A together with the atoms marked a and b represents the following ring:

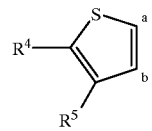

wherein R⁴ is hydrogen and R⁵ is as defined above.

k) transforming a compound of formula (XIX):

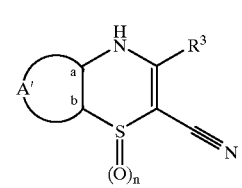

(XIX)

wherein A' together with the atoms marked a and b represents a ring selected from

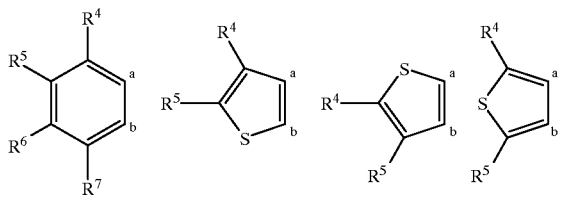

and $R^3$ $R^4$, $R^5$, $R^6$, $R^7$ and n are as defined above, to a compound of formula (I),

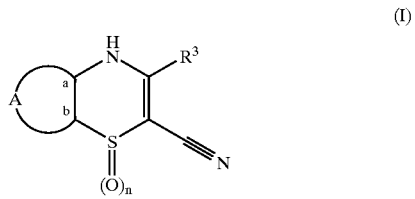

(I)

wherein A, $R^3$ and n are as defined above, by chemically modifying the substitution of the A'-ring by classical methods by modifying substituents or by introducing new substituents, e.g. by halogenation, electrophilic aromatic substitution, nucleophilic aromatic substitution, cross coupling, oxidation or reduction.

The starting materials are either known compounds or compounds which may be prepared in analogy with the preparation of known compounds or in analogy with known methods as described by e.g. El-Taweel et al., *Arch. Pharmacol. Res.*, 13, 261–264 (1990), Liso et al., *Synthesis*, 1983, 755–757, Kano et al., *Heterocycles*, 12, 681–684 (1979), C. Bieniarz and M. J. Cornwell, *Tetrahedron Lett*, 34 (6) 939–942 (1993), Sharpe, C. J. et al., *J. Med. Chem.*, 15, 1972, 523–529, P Petitcolas, et al., *Bull Soc Chim Fr*, 1949, 103, Paulmier, Claude, *Bull. Soc. Chim. Fr.*, 2 (3–4) 1980, 151–156, Gewald, K.; Hain, U.; Madlenscha, M., *J. Prakt. Chem.*, 330 (6) 1988, 866–872, Laimer, Ingrid; Erker, Thomas, *Liebigs Ann. Org. Bioorg. Chem.*, 2, 1995, 453–456, Puschmann, I.; Erker, T., *Monatsh. Chem.*, 126, 5, 1995, 569–578, Puschmann, Isolde; Erker, Thomas, *Heterocycles*, 36, 6, 1993, 1323–1332, Puschmann, Isolde; Erker, Thomas, *Heterocycles*, 41, 4, 1995, 709–720, Garanti, L. et al., *J. Heterocycl. Chem.*, 13, 1976, 1339–1341, Carmellino, M. L.; Massolini, G., *Farmaco Ed. Sci.*, 42, 12, 1987, 979–986, Kay, David P.; Kennewell, Peter D.; Westwood, Robert, *J. Chem. Soc. Perkin Trans. 1*, 8, 1982, 1879–1884, Bost et al., *J. Am. Chem. Soc.*, 73, 1951 (1968), M. P. Sammes and R. L. Harlow, *J. Chem. Soc., Perkin Trans. 2*, 1971, 1130–1135, T. Kotani et al., *Chem. Pharm. Bull.* 45, 297–304 (1 997), B. L. Mylari et al., *J. Med. Chem.* 34, 108–122 (1991).

PHARMACOLOGICAL METHODS

The ability of the compounds to interact with potassium channels can be determined by various methods.

Potassium channel modulators may be studied using the inside-out and whole-cell configurations of the patch-clamp technique (Hamill et al., *Plügers Arch.*, 391, 85–100 (1981)). This method allows the direct study of the activity of ion channels from primary cells, cell lines, cells transfected with and oocytes expressing the ion channel of interest. Whole-cell recordings contain the summed activity of all ion channels in the cell and is a reliable measure of the degree of channel activation or inhibition. Inside-out patches allow the recording of a single or a few individual ion channels thereby giving more information on the mechanism (s) of action of the drug(s) tested.

The activity of the compounds as potassium channel openers can also be measured as relaxation of rat aorta rings according to the following procedure:

A section of rat thoracic aorta between the aortic arch and the diaphragm was dissected out and mounted as ring preparations as described by Taylor P. D. et al, *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

In the pancreatic b-cell the opening of the $K_{ATP}$-channels can be determined by measuring the subsequent change in the concentration of cytoplasmic free $Ca^{2+}$ concentration according to the method of Arkhammar P. et al., *J. Biol. Chem.*, 262, 5448–5454 (1987).

$^{86}Rb^+$ Efflux from a β-cell Line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/ml $^{86}Rb^+$ and replated into microtiter plates (96 well cluster 3596, sterile, from Costar Corporation, MA, USA) at a density of 50000 cells/well in 100 μl/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty μl Ringer buffer and 1 μl control- or test compound dissolved in DMSO was added. After incubation 1 h at room temperature with a lid, 50 μl of the supernatant was transferred to PicoPlates (Packard Instrument Company, CT, USA) and 100 μl MicroScint40 (Packard Instrument Company, CT, USA) added. The plates were counted in TopCount (Packard Instrument Company, CT, USA) for 1 min/well at the $^{32}P$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}=c$ and $E_{max}=d$, when the curve is turned of at infinite concentrations.

The effect of $K_{ATP}$-channel modulators on pancreatic beta-cells can be determined by measuring qualitative changes in membrane potential in the insulin producing cell line β-TC3 using fluorescence imaging techniques.

The slow fluorescent membrane potential probe DiBAC was used. The cells were kept in $Ca^{2+}$-HEPES buffer supplemented with 10 mM glucose. After 5 s of each 60 s run the compound was added. 48 wells were run in each set, taking about 1 h. The same cells were then run again, now adding 25 mM KCl after 5 s, and the depolarisation-induced increase in DiBAC fluorescence monitored for 55 s.

In addition the effect of $K_{ATP}$-channel modulators on pancreatic beta-cells can be determined by measuring the increase or decrease in insulin release from insulin producing beta-cell lines or isolated islets.

Effect of $K_{ATP}$-channel modulators can be measured using the following procedure:

- The beta cells are cultured with change of media every three-four days.
- Cells are then seeded in 96 well microtiter dishes and cultured for three day at 38° C., 5% $CO_2$ and 95% humidity.
- The cells are washed with NN-buffer (+10 mM Hepes+ 0.1% BSA) for one minute and glucose (final conc. 22 mM), IBMX (final conc. 0.1 mM) and compounds (final conc. from $5\times10^{-5}$ M–$5\times10^{-8}$ M) added. All cells are then incubated for three hours (38° C., 5% $CO_2$ and 95% humidity).
- Supernates are harvested into Greiner minisorb microtiter wells and frozen. Insulin is measured using elisa-techniques.

The compounds of the present invention show high potency in the insulin release test and high selectivity compared to the relaxation of rat aorta rings test.

PHARMACEUTICAL COMPOSITIONS

The present invention also relates to pharmaceutical compositions comprising, as an active ingredient, at least one of the compounds of the general formula I or a pharmaceutically acceptable salt there of and, usually, such compositions also contain a pharmaceutically acceptable carrier or diluent.

Pharmaceutical compositions comprising a compound of the present invention may be prepared by conventional techniques, e.g. as described in Remington: *The Science and Practise of Pharmacy*, 19$^{th}$ Ed., 1995. The compositions may appear in conventional forms, example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinyl pyrrolidone. Similar, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, topical, ophthalmic solution or an oinment, oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suiatable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| | |
|---|---|
| Active compound | 5.0 mg |
| Laotosum | 67.8 mg Ph.Eur. |
| Avioel ® | 31.4 mg |
| Amberlite ® | 1.0 mg |
| Magnesii stearas | 0.25 mg Ph.Eur. |

The compounds of the invention may be administered to a mammal, especially a human, in need of such treatment, prevention, elimination, alleviation or amelioration of various diseases as mentioned above and especially of diseases of the endocrinological system such as hyperinsulinaemia and diabetes. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds according to the invention are effective over a wide dose range. For example, in the treatment of humans, dosages from about 0.05 to about 1000 mg, preferably from about 0.1 to about 500 mg of a compound of formula I, conveniently given from 1 to 5 times per day. A most preferable dosage is about 1 mg to about 100 mg per day. The exact dosage will depend upon the mode of administration, form in which administered, the subject to be treated and the body weight of the subject to be treated, and the preference and experience of the physician or veterinarian in charge.

Generally, the compounds are dispensed in unit dosage form comprising from about 1 to about 100 mg of the compounds of formula I in or together with a pharmaceutically acceptable carrier per unit dosage.

Usually, dosage forms suitable for oral, nasal, pulmonal or transdermal administration comprise from about 0.05 mg to about 1000 mg, preferably from about 0.1 mg to about 500 mg of the compounds of formula I admixed with a pharmaceutically acceptable carrier or diluent.

Any novel feature or combination of features described herein is considered essential to this invention.

EXAMPLES

Providing the compounds of the invention is further illustrated in the following examples which, however, are not to be construed as limiting.

Example 1

7-Chloro-3-methyl-4H-1,4-benzothiazine-2-carbonitrile 1,1-dioxide a) 2-Acetylamino-5-chloro-benzenesulfinic acid 2-Acetylamino-5-chloro-benzenesulfonyl chloride was prepared from 2-acetylamino-5-chloro-benzenesulfonic acid pyridinium salt according to Barco et al., *Synthesis* 1974, 877, and was immediately reduced to the title compound by treatment with 4-methylbenzenethiol and triethylamine according to the general method described by Lee and Field, *Synthesis*, 1990, 391. The crude product was practically pure and was used without purification; mp 116–119° C.; $^1$H-NMR (DMSO-d$_6$) δ (ppm): 10.07 (br, 1H), 7.7–7.48 (m, 3H), 5.7 (br, —SO$_2$H+H$_2$O), 2.08 (s, 3H); IR (KBr) ν (cm$^{-1}$): 3236, 1530, 1082, 1045.

b) N-(4-Chloro-2-cyanomethylsulfonylphenyl)acetamide

Sodium hydride (0.10 g, 60% dispersion in mineral oil) was added at ambient temperature under nitrogen in small portions to a stirred solution of 2-acetylamino-5-chloro-benzenesulfinic acid (0.55 g) in dry dimethylformamide. After stirring for 35 min iodoacetonitrile (0.18 ml) was added and the temperature was raised to 70° C. for 45 min. Then the solvent was removed in vacuo. The residue was triturated with water (30 ml) and filtered. The filter cake was dried, stirred with a mixture of ether (5 ml) and petroleum ether (10 ml) for 1 h, filtered off and dried to give the title compound as white needles. Yield 0.52 g (81%), mp 173.5–174° C., $^1$H-NMR(DMSO-d$_6$) δ (ppm): 9.69 (s, 1H); 8.06–7.87 (m, 3H); 5.37 (s, 2H), 2.16 (s, 3H); $^{13}$C-NMR (DMSO-d$_6$) δ (ppm): 169.6, 136.6, 136.4, 130.5, 129.8, 129.5, 128.5, 112.0, 44.9, 24.3; IR(KBr) ν (cm$^{-1}$): 3343 (NH), 2258(CN), 1682(C=O), 1330(SO$_2$), 1156 and 1140 (SO$_2$).

c) 7-Chloro-3-methyl-4H-1,4-benzothiazine-2-carbonitrile 1,1-dioxide

N-(4-Chloro-2-cyanomethylsulfonylphenyl)acetamide (0.73 g) was added at room temperature to 0.5 M aqueous NaOH (10 ml) to form a yellow solution. After 45 min 0.1 g of charcoal was added and the mixture was filtered through celite. The filtrate was cooled to 0° C. and 1 M HCl (7.5 ml) was added. After 30 min the precipitate was collected by filtration and dried to give 0.66 g of the title compound. Recrystallization from methanol gave pale crystals. Yield 0.45 g (66%); mp 297–299° C.; $^1$H-NMR(CD$_3$OD) δ (ppm): 7.91 (d, J=2.8 Hz, 1H); 7.68 (dd, 1H); 7.37 (d, J=9 Hz, 1H); 4.88 (br, H$_2$O+NH); 2.51 (s, 3H); $^{13}$C-NMR (DMSO-d$_6$) δ (ppm): 155.9, 134, 133.9, 129.6, 125.0, 121.40, 121.36, 112.7, 85.7, 20.3. IR (KBr) ν (cm$^{-1}$): 3259, 3176, 3100, 2214, 1531, 1482, 1305, 1144. An additional crop of the title compound (0.09 g, 13%) was obtained from the mother liqueor.

Example 2

3-Methyl-6-trifluoromethyl-4H-1,4-benzothiazine-2-carbonitrile 1,1-dioxide a) (2-Amino-4-trifluoromethylphenylsulfanyl)acetonitrile Sodium hydride (2.93 g, 60% dispersion in mineral oil) was added at 5–10° C. under nitrogen in small portions to a stirred and cooled solution of 2-amino-4-trifluoromethyl-benzenethiol (8.00 g) dissolved in dry dimethylformamide (125 ml). After stirring for 45 min iodoacetonitrile (2.65 ml) was added. Stirring was continued at ~0° C. for 15 min and then at room temperature for 1 h. The mixture was concentrated in vacuo at 55° C. and the oily residue was extracted with petroleum ether (3×50 ml) in order to remove the mineral oil. The residue was partitioned between water (50 ml) and ethyl acetate (100 ml). The organic phase was washed with water (2×50 ml) and then with brine (30 ml), dried over sodium sulfate, filtered and concentrated in vacuo to give a yellow oil. The crude product was purified by flash chromatography on silica gel eluted with ethyl acetate-heptane 3:7 giving the title compound as a yellow oil. Yield 6.1 g (75%); $^1$H-NMR (DMSO-d$_6$) δ (ppm): 7.54 (d, J=8.3 Hz, 1H), 7.09 (d, J=1.8 Hz, 1H), 6.86 (dd, 1H), 5.97 (br, 2H), 4.02 (s, 2H); $^{13}$C-NMR (DMSO-d$_6$) δ (ppm): 150.0, 135.7, 130.8 (q, J=31 Hz), 124.2 (q, J=272 Hz), 117.7, 117.1, 112.1 (q, J=3.8 Hz), 110.6 (q, J=3.9 Hz), 18.1.

b) N-(2-Cyanomethylsulfanyl-5-trifluoromethylphenyl)acetamide (2-Amino-4-trifluoromethylphenylsulfanyl)acetonitrile (0.66 g) was stirred on an ice bath at 0° C. Acetic acid anhydride (2.5 ml) was added, and the resulting solution was allowed to reach room temperature. After 1 h the mixture was concentrated in vacuo and the solid residue was triturated with petroleum ether (2×2 ml), filtered off and and dried to give the title compound as a white solid. Yield 0.75 g (96%), mp 103–103.3° C.; $^1$H-NMR(CDCl$_3$) δ (ppm): 8.79 (br, 1H), 8.36 (br, 1H), 7.78 (d, 1H), 7.38 (dd, 1H, J: 8 Hz/2 Hz), 3.50 (s, 2H) 2.29 (s, 3H); $^{13}$C-NMR (DMSO-d$_6$) δ (ppm): 169.2 (C=O), 137.1, 134.3, 129.6, 127.7 (q, J=32 Hz), 122.7 (m, 2C), 123.9 (CF$_3$, J=272), 117.6 (CN), 23.2 (H$_3$), 17.6 (CH$_2$); IR (KBr) ν (cm$^{-1}$): 3249, 2244 (C≡N), 1660, 1530, 1483, 1335, 1170, 1116, 1095.

c) N-(2-Cyanomethylsulfonyl-5-trifluoromethylphenyl) acetamide

A solution of 3-chloroperbenzoic acid (0.78 g, purity ~70%) in dichloromethane was added to a stirred solution of N-(2-cyanomethylsulfanyl-5-trifluoromethylphenyl) acetamide (0.31 g) in dichloromethane (10 ml) at 0° C. After 6½ h an additional amount of 3-chloroperbenzoic acid (0.2 g) was added and the solution was left at room temperature overnight. Excess of peracid was destroyed by washing the reaction mixture with a solution of sodium disulfite (0.5 g) in water (10 ml). The solution was dried over sodium sulfate and evaporated. The residue was recrystallized from 96% ethanol to give the title compound as white voluminous crystals. Yield 0.22 g (62%); mp 146–147° C. An additional crop of the title compound (0.05 g, 14%) was obtained from the mother liqueor. $^1$H-NMR(CDCl$_3$) δ (ppm): 9.54 (br, 1H, NH), 9.00 (br, 1H), 8.10 (d, J=8.3 Hz, 1H), 7.55 (dd, J1=8.3 Hz, J2=1.4 Hz, 1H), 4.18 (s, 2H), 2.30 (s, 3H); $^{13}$C-NMR (CDCl$_3$) δ (ppm): 168.8 (C=O), 139.1, 138.6 (J=34 Hz), 131.6, 125.7, 122.6 (CF$_3$, J=274 Hz), 120.6 (J=3.7 Hz), 120.2 (J=4.0 Hz), 109.3 (C≡N), 45.9 (CH$_2$), 25.3 (CH$_3$); MS m/e (rel. intensity): 306 (8%, M$^+$), 264 (55%), 224 (35%), 202 (7.6%), 183 (5%), 176 (12%), 160 (28%), 140 (6%), 43 (100%).

d) 3-Methyl-6-trifluoromethyl-4H-1,4-benzothiazine-2-carbonitrile 1,1-dioxide

The title compound was prepared by base catalyzed ring closure of N-(2-cyanomethylsulfonyl-5-trifluoromethylphenyl)-acetamide by a procedure analogous to the procedure described in EXAMPLE 1 c); white flakes (from methanol), mp 329–333° C., $^1$H-NMR(CD$_3$OD) δ (ppm): 8.20–8.10 (br d, 1H), 7.78–7.62 (m, 2H), 4.88 (br, H$_2$O+NH), 2.52 (s, 3H); $^{13}$C-NMR (DMSO-d$_6$) δ (ppm): 156.4, 135.6, 133.1 (q, J=33 Hz), 126.6, 124.2, 123.0 (CF$_3$, J=273 Hz), 121.9 (J=3.4 Hz), 116.2 (J=4.5 Hz), 112.4 ( C≡N), 86.3 20.4; IR (KBr) ν (cm$^{-1}$): 3301, 3195, 3133, 2214(C≡N), 1628, 1614, 1592, 1554, 1487, 1422, 1339, 1308, 1265, 1241, 1187, 1159, 1131, 1083, 890; MS m/e (rel. intensity): 288 (74%, M$^+$), 224 (74%), 223 (100%), 203 (8%), 155 (9%), 69 (16%).

Example 3

3-Methyl-6-trifluoromethyl-4H-1,4-benzothiazine-2-carbonitrile 1-oxide a) N-(2-Cyanomethylsulfinyl-5-trifluoromethylphenyl)acetamide A solution of N-(2-cyanomethylsulfanyl-5-trifluoromethylphenyl)acetamide(0.42 g) in dioxane (2.50 ml) was added dropwise to a stirred solution of sodium periodate (0.69 g) in a mixture of water (6 ml) and dioxane (1.50 ml) at ambient temperature. An additional amount of dioxane (2.50 ml) was added. The mixture was stirred at 40° C. for 6½ h, then at room temperature overnight. A precipitate was removed by filtration and washed on the filter with dichlorometane (20 ml). The two phases of the filtrate were shaken and separated. The aqueous phase was extracted with dichloromethane (2×10 ml). The combined organic phases were dried over sodium sulfate, filtered and concentrated in vacuo. The more polar component of the residue was isolated by flash chromatography on silica gel eluted with 1) ether and 2) ethyl acetate to give a slowly crystallizing oil. Trituration with petroleum ether and subsequent drying gave white crystals. Yield 0.16 g (38%); mp 149–151° C.; $^1$H-NMR(CDCl$_3$) δ (ppm): 9.9 (br, 1H), 8.70 (d, J=2 Hz, 1H), 7.68–7.46 (d+dd, J=8Hz and 8 Hz/2 Hz, 1H+1H), ABX-system at 4.13 (d, J=16 Hz, 1H) and 3.98 (d, J=16 Hz, 1H), 2.25 (s, 3H); $^{13}$C-NMR (DMSO-d$_6$) δ (ppm): 170.1, 141.3, 135.8, 132.7 (q, J=32 Hz), 127.0, 123.5 (CF$_3$, J=273 Hz), 123.1 (J=3.6 Hz), 122.0 (J=3.6 Hz), 113.3 (C≡N), 42.6 (CH$_2$), 23.2 (CH$_3$); IR (KBr) ν (cm$^{-1}$): 3220 (NH), 2252 (C≡N), 1691 (C=O), 1532, 1476, 1337, 1273, 1176, 1128, 1033, 888, 675.

b) 3-Methyl-6-trifluoromethyl-4H-1,4-benzothiazine-2-carbonitrile 1-oxide

The title compound was prepared by base catalyzed ring closure of N-(2-cyanomethylsulfinyl-5-trifluoromethylphenyl)acetamide by a procedure analogous to the procedure described in EXAMPLE 1 c); white crystals, mp 290–292° C. (dec., ebulition); $^1$H-NMR (DMSO-d$_6$) δ (ppm): 12.4 (br, 1H, NH), 8.30–8.20 (1H; ~d, J 8.3 Hz at 8.25), 7.91–7.72 (2H; ~d, J 1.4 Hz at 7.86 and dd at 7.78), 3.35 (H$_2$O), 2.59 (s, 3H, CH$_3$); $^{13}$C-NMR (DMSO-d$_6$) δ (ppm): 153.5, 133.7, 132.4 (J=33 Hz), 132.0, 126.3, 123.3 (CF$_3$, J=273 Hz), 121.6 (J=3.4 Hz), 118.1 (C≡N), 115.9 (J=4.1 Hz), 85.3, 20.4; MS, m/e (rel. intensity): 272 (18%, M$^+$), 256 (8%), 224 (100%), 223 (63%), 202 (8%); IR(KBr) ν (cm$^{-1}$): 3269, 3122, 3081, 3084, 3034, 2201 (C≡N), 1629, 1614, 1587, 1535, 1482, 1419, 1336, 1304, 1238, 1185, 1164, 1140, 1056, 1014, 888, 835.

Example 4

3-Phenyl-4H-1,4-benzothiazine-2-carbonitrile 1,1-dioxide

A mixture of 3-phenyl-4H-1,4-benzothiazine-2-carbonitrile (0.10 g, prepared according to Liso et al., *J. Heterocycl. Chem.* 18, 279 (1981), Liso et al., *Synthesis* 1983, 755) and acetic acid (6 ml) was added to a stirred solution of potassium permanganate (88 mg) in water (10 ml) at ambient temperature. After 2 h, 3 h and 18 h additional amounts (25 mg, 40 mg and 40 mg) of potassium permanganate were added. Then a 40% solution of sodium hydrogensulfate (200 µl) was added. After stirring for ½ h the mixture was filtered through celite. The filtrate was extracted with ethyl acetate (2×25 ml). The combined extracts were dried over sodium sulfate, filtered and concentrated in vacuo to give a solid. Trituration with ethyl acetate (2 ml), filtration and drying gave the title compound as light yellow crystals. Yield 34 mg (38%); mp 286–289° C.; $^1$H-nmr(DMSO) δ (ppm): 12.21 (br, 1H), 8.07–7.97 (m, 1H), 7.84–7.5 (m, 8H); IR(KBr) ν (cm$^{-1}$): 3298 (NH), 2198 (C≡N), 1598, 1554, 1514, 1476, 1433, 1301, 1171, 1154, 1136; MS m/e (rel. intensity): 282 (25 %, M$^+$), 250 (4%), 218 (100%), 190 (15%), 115 (10%), 77 (10%).

Example 5

3-Phenyl-4H-1,4-benzothiazine-2-carbonitrile 1-oxide

A mixture of 3-phenyl-4H-1,4-benzothiazine-2-carbonitrile (0.10 g) and 3-chloroperbenzoic acid (0.17 g, purity 80%) in dichloromethane (8 ml) was stirred at 0° C. for 30 min. The mixture was filtered and the filter cake was washed with dichloromethane and dried to give the title compound as pale crystals. Yield 66 mg; mp 182–184° C.; $^1$H-nmr(DMSO) δ (ppm): 12.31 (br, 1H), 8.09–7.99 (m, 1H), 7.83–7.60 (m, 7H), 7.60–7.48 (m, 1H); IR(KBr) ν (cm$^{-1}$): 3211, 3161, 2985, 2935, 2850, 2193 (C≡N ), 1603, 1548, 1502, 1463, 1429, 1004, 771, 703; MS m/e (rel. intensity): 250 (86%; M$^+$-16), 249 (87%), 218 (39%), 211 (100%), 190 (11%), 146 (23%), 108 (43%), 69 (43%).

Example 6

3,7-Dimethyl-4H-thieno[3,2-b]-1,4-thiazine-2-carbonitrile 1,1-dioxide a) (2-Amino-4-methylthiophene-3-sulfonyl)acetonitrile A mixture of 2,5-dihydroxy-2,5-dimethyl-1,4-dithiane (3.00 g), sulfonyldiacetonitrile (SO$_2$(CH$_2$CN)$_2$, 4.36 g) and 4-dimethylaminopyridine (0.3 g) in anhydrous methanol (30 ml) was stirred at reflux for 3 h. The mixture was cooled to room temperature, water (130 ml) was added and the resulting mixture was extracted with ethyl acetate (3×50 ml). The combined extracts were washed with brine (20 ml), dried over sodium sulfate, filtered and evaporated to give a dark, oily residue. The title compound was separated from the more polar components by flash chromatography on silica gel eluted with ethyl acetate-heptane 1:1 and was obtained as pale crystals. Yield 2.70 g (38%); mp 88–90° C.; $^1$H-NMR(CDCl$_3$) δ (ppm): 6.01 (s, 1H), 5.86 (br, 2H), 4.07 (s, 2H), 2.31 (s, 3H); $^{13}$C-nmr(CDCl$_3$) δ (ppm): 164.4, 134.4, 111.1, 107.5, 105.4, 45.7, 17.1; MS m/e (rel. intensity): 216 (35%, M$^+$), 176 (23%), 128 (100%), 112 (26%), 85 (10%), 68 (28%); IR(KBr) ν (cm$^{-1}$): 3476, 3367, 2991, 2260, 1599, 1498, 1322, 1150, 1114.

b) 3,7-Dimethyl-4H-thieno[3,2-b]-1,4-thiazine-2-carbonitrile 1,1-dioxide

A solution of (2-amino-4-methylthiophene-3-sulfonyl) acetonitrile (0.50 g) in trimethyl orthoacetate (1 ml) was heated at 120–130° C. for 2 h and then concentrated in vacuo at ~50° C. for 1 h. The residue was suspended in a mixture of absolute ethanol (5 ml) and triethylamine (0.32 ml) and stirred at reflux for ½ h, then at 0° C. for ½ h and filtered. The filtrate was heated at reflux for one more hour, concentrated in vacuo, dissolved in ethyl acetate (10 ml) and extracted with 1 M NaOH (10 ml). The aqueous phase was washed with ethyl acetate (2×5 ml), cooled to 0° C. and acidified with 10 M HCl, pH being adjusted to 0–1. After stirring for 1 h at 0° C. the precipitate was collected by filtration and dried to give the title compound as a practically pure beige solid. Yield 0.09 g (16%). An analytically pure sample was obtained by recrystallization from methanol; mp 347–349° C. (decomp.); $^1$H-NMR(DMSO-d$_6$) δ (ppm): 12.7 (br, 1H), 7.09 (s, 1H), 2.40 (s, 3H), 2.32 (s, 3H); $^{13}$C-NMR (DMSO-d$_6$) δ (ppm): 153.9, 143.5, 131.5, 119.6, 116.6, 113.8, 89.6, 20.4, 15.3; IR 3226, 3030, 2903, 2227(C≡N), 1580, 1526, 1281 and 1134 (SO$_2$). Elemental analysis, % found (calc. for C$_9$H$_8$N$_2$O$_2$S$_2$): C 44.69 (44.98); H 3.22 (3.36); N 11.33 (11.66); S 26.76 (26.69).

Example 7

3-Propyl-6-trifluoromethyl-4H-1,4-benzothiazine-2-carbonitrile 1,1-dioxide a) N-(2-Cyanomethylsulfanyl-5-trifluoromethylphenyl)-butyramide (2-Amino-4-trifluoromethylphenylsulfanyl)acetonitrile (1.33 g) dissolved in dichloromethane (5 ml) was stirred on an ice bath at 0° C. Diisopropylethylamine (1 ml) and butyric acid chloride (0.9 ml) was added, and the resulting solution was allowed to reach room temperature. After 22 h more butyric acid chloride (0.9 ml) and DMAP (0.70 g) were added at 0° C. and stirring was continued at 40° C. for 24 h. The cold mixture was diluted with dichloromethane (20 ml), extracted with saturated aqueous sodium bicarbonate (10 ml), washed with water (2×50 ml), dried (Na$_2$SO$_4$) and concentrated in vacuo. The residue was purified by flash chromatography using ethyl acetate/heptane 1:1 as eluent. The title compound was obtained as a sirup. Yield 1.72 g (100%). The compound could be crystallised from ethyl acetate/heptane, mp 88.5–89.5° C.; El SP/MS: 302 (M+). $^1$H-NMR(CDCl$_3$) δ (ppm): 8.85 (br, 1H), 8.38 (br, 1H), 7.28 (d, 1H), 7.38 (dd, 1H), 3.50 (s, 2H), 2.46 (t, 2H), 1.82 (sextet), 1.03 (t, 3H).

b) N-(2-Cyanomethylsulfonyl-5-trifluornmethylphenyl) butyramide

To a solution of N-(2-cyanomethylsulfanyl-5-trifluoromethylphenyl)butyramide(1.11 g) in acetic acid (8 ml) at 0° C. was added hydrogen peroxide (35%, 4 ml) dropwise. After 1½ h at room temperature and 20 h at 60° the reaction mixture was cooled and a small amount of water was added. The precipitate was collected by filtration and washed with water. Recrystallization from 96% ethanol gave the title compound as white crystals. Yield 0.44 g (36%); mp 126–127° C. El SP/MS: 334 (M+). $^1$H-NMR(CDCl$_3$) δ (ppm): 9.55 (br, 1H, NH), 9.04 (br, 1H), 8.08 (d, 1H), 7.52 (dd, 1H), 4.14 (s, 2H), 2.48 (t, 2H), 1.80 (sexset, 2H), 1.03 ppm (t, 3H).

c) 3-Propyl-6-trifluoromethyl-4H-1,4-benzothiazine-2-carbonitrile 1,1-dioxide

N-(2-Cyanomethylsulfonyl-5-trifluoromethylphenyl) butyramide (0.41 g) in 0.5 M aqueous NaOH (5 ml) was stirred at room temperature for 2 h. The mixture was cooled to 0° C. and 1M HCl (4 ml) was added. After 30 min the precipitate was collected by filtration and dried to give 0.33 g (85%) of the title compound; mp 199.5–200.5° C.; El SP/MS: 316 (M+); $^1$H-NMR(CD$_3$OD) δ (ppm): 8.16 (d, 1H); 7.73 (d+s, 2H); 4.88 (br, H$_2$O+NH); (dd, 2H), 1.88 (sextet, 2H), 1.06 ppm (t, 3H).

Example 8

5,7-Difluoro-3-methyl-4H-1,4-benzothiazine-2-carbonitrile 1,1-dioxide a) (2-Amino-3,5-difluoro-phenylsulfanyl)acetonitrile A suspension of 2-amino-4,6-difluoro-benzothiazole (7.00 g) was stirred for 6 h at 160° C. under nitrogen in a solution of potassium hydroxide (12.6 g) in water (20 ml). The resulting mixture was cooled to 0–5° C. and a solution of acetic acid (8.85 ml) in water (10 ml) and subsequently ethanol (40 ml) and iodoacetonitrile (2.75 ml) were added. After 30 min the mixture was neutralized with acetic acid (2.25 ml) and filtered. The filtrate was evaporated to approx. 30 ml and diluted with water (150 ml). A yellow precipitate was filtered off and dried. The crude product was purified by flash chromatography on silica gel eluted with ethyl acetate—heptane (3:7) yielding the title compound, R$_f$=0.26, as orange crystals, mp 66–67° C.; $^1$H-NMR (DMSO-d$_6$), δ (ppm): 7.30–7.07 (m, 2H, Ar—H), 5.33 (br, 2H, NH$_2$), 4.05 (s, 2H, CH$_2$).

b) N-(2-Cyanomethylsulfanyl-4,6-difluoro-phenyl) acetamide

Acetyl chloride (575 μl, 8 mmol) in THF (2 ml) and subsequently pyridine (645 μl, 8 mmol) in THF (2 ml) were added to a stirred solution of (2-amino-3,5-difluorophenylsulfanyl)acetonitrile (1.53 g) in THF (20 ml) at 0° C. The mixture was stirred at 0° C. for 15 min, then at ambient temperature for 1 h. Additional amounts of acetyl chloride (57 μl) and pyridine (65 μl) were added, and stirring was continued for 1 h. Then the solvent was removed in vacuo and the residue was triturated with water (25 ml). The precipitate was filtered off and dried. Recrystallization from 96% ethanol gave the title compound. Yield 1.16 g (63%), mp 148.5–149° C. An additional crop of the title compound (0.25 g, 13%) was obtained from the mother liqueor; $^1$H-NMR (DMSO-d$_6$), δ (ppm): 9.65 (s, 1H, NH), 7.40–7.20 (m, 2H, Ar—H), 4.34 (s, 2H, CH$_2$), 2.09 (s, 3H, CH$_3$).

c) N-(2-Cyanomethylsulfonyl-4,6-difluoro-phenyl) acetamide

N-(2-Cyanomethylsulfanyl-4,6-difluoro-phenyl) acetamide (0.25 g) was suspended in glacial acetic acid (2 ml). Hydrogen peroxide (35%, 1 ml) was added and the mixture stirred at 100° C. for 1 h 45 min. Then the mixture was cooled to 0° C. and water (5 ml) was added. After stirring for ½ h a white precipitate was isolated by filtration, washed with water and dried to give the title compound as white needles. Yield 0.17 g (61%); $^1$H-NMR (DMSO-d$_6$), δ (ppm): 9.81 (br s, 1H, NH), 8.08–7.90 (m, 1H, Ar—H), 7.80–7.65 (m, 1H, Ar—H), 5.23 (s, 2H, CH$_2$), 2.10 (s, 3H, CH$_3$).

d) 5,7-Difluoro-3-methyl-4H-1,4-benzothiazine-2-carbonitrile 1,1-dioxide N-(2-Cyanomethylsulfonyl-4,6-difluoro-phenyl)acetamide (0.83 g) was dissolved in 0.5 M NaOH (10 ml) at room temperature. After 1 h the mixture was filtered. The filtrate was cooled to 0° C. and 1M HCl (7.5 ml) was added. After 10 min at 0° C. a white precipitate was isolated by filtration, washed with water (5 ml) and dried. Recrystallization from methanol gave the pure title compound as voluminous white needles. Yield 0.39 g (49%); mp 289–290° C.; $^1$H-NMR (DMSO-d$_6$), δ (ppm): 11.9 (br s, 1H, NH), 8.03–7.73 (m, 2H), 2.50 (s, CH$_3$+DMSO), IR (KBr) ν (cm$^{-1}$): 3260 (NH), 2216 (C≡N).

Example 9

7-Fluoro-3-methyl-4H-1,4-benzothiazine-2-carbonitrile 1,1-dioxide a) (2-Amino-5-fluoro-phenylsulfanyl)acetonitrile A suspension of 2-amino-6-fluoro-benzothiazole (5.13 g) was stirred for 6½ h at 165–170 °C. under nitrogen in a solution of potassium hydroxide (10.3 g) in water (20 ml). The resulting mixture was cooled to 10° C. and adjusted to pH ~8 by adding acetic acid, keeping the temperature below 25° C. The mixture was cooled to 10° C. and ethanol (30 ml) and iodoacetonitrile (2.20 ml) were added. After stirring for 15 min acetic acid (1.8 ml) was added and approx. half of the solvent was removed in vacuo. The residue was diluted with water (150 ml) and extracted with ethyl acetate (50 ml). The extract was dried over sodium sulfate, filtered and evaporated to give the title compound as a practically pure yellow oil. Yield 4.88 g (88%); $^1$H-NMR (DMSO-d$_6$), δ (ppm): 7.26–7.14 (m, 1H, Ar—H), 7.09–6.95 (m, 1H, Ar—H), 6.85–6.72 (m, 1H, Ar—H), 5.36 (br, 2H, NH$_2$), 3.99 (s, 2CH$_2$).

b) N-(2-Cyanomethylsulfanyl-4-fluoro-phenyl)acetamide

Acetyl chloride (1.9 ml) in THF (10 ml) and subsequently pyridine (2.15 ml) in THF (10 ml) was added to a stirred solution of (2-amino-5-fluoro-phenylsulfanyl)acetonitrile (4.39 g) in THF (40 ml) at 0° C. The mixture was stirred at 0° C. for 1 h. Then the solvent was removed in vacuo and the residue was triturated with water (100 ml). The precipitate was filtered off and dried. Crude yield 4.45 g (82%); mp 97–100° C. The title compound could be further purified by recrystallization from 96% ethanol; mp 100.5–101.5° C.; $^1$H-NMR (DMSO-d$_6$), δ (ppm): 9.68 (s, 1H, NH), 7.50–7.30 (m, 2H, Ar—H), 7.23–7.07 (m, 1H, Ar—H), 4.26 (s, 2H, CH$_2$), 2.05 (s, 3H, CH$_3$); IR (KBr) ν (cm$^{-1}$): 3239 (NH), 2244 (C≡N), 1641 and 1579 (amide).

c) N-(2-Cyanomethylsulfonyl-4-fluoro-phenyl)acetamide

N-(2-Cyanomethylsulfanyl-4-fluoro-phenyl)acetamide (0.43 g) was suspended in glacial acetic acid (2 ml). Hydrogen peroxide (35%, 1 ml) was added and the mixture was stirred at 100° C. for 1 h. Then the mixture was cooled to 0° C. and water (15 ml) was added. After stirring for 10 min a white precipitate was isolated by filtration, washed with water and dried. Recrystallization from 96% ethanol afforded the title compound as white needles, mp 154–157° C.; yield 0.28 g (58%); $^1$H-NMR (DMSO-d$_6$), δ (ppm): 9.64 (s, 1H, NH), 7.99–7.64 (m, 3H, Ar—H), 5.30 (s, 2H, CH$_2$), 2.08 (s, 3H, CH$_3$).

d) 7-Fluoro-3-methyl-4H-1,4-benzothiazine-2-carbonitrile 1,1-dioxide

N-(2-Cyanomethylsulfonyl-4-fluoro-phenyl)acetamide (0.21 g) was dissolved in 0.5 M NaOH (3 ml) at room temperature. After 1½ h the mixture was filtered. The filtrate was cooled to 0° C. and 4M HCl (0.5 ml) was added. A white precipitate was isolated by filtration, washed with water (5 ml) and dried to give the title compound as a white solid. Yield 0.17 g (85%); mp 326–327° C. (decomp.); $^1$H-NMR (DMSO-d$_6$), δ (ppm): 12.07 (s, 1H, NH), 7.95–7.81 (m, 1H, Ar—H), 7.75–7.45 (m, 2H, Ar—H), 2.47 (s, CH$_3$ +DMSO); IR (KBr) ν (cm$^{-1}$): 3291 (NH), 2214 (C≡N).

Example 10

3-Methyl-7-methoxy-4H-1,4-benzothiazine-2-carbonitrile 1,1-dioxide a) N-(2-Cyanomethylsulfanyl-4-methoxyphenyl)acetamide Sodium borohydride (0.19 g) was added in small portions over 30 min to a stirred solution of bis(2-acetylamino-5-methoxyphenyl)disulfane(1.0 g, Hodgson; Handley, *J. Chem. Soc.*, 1928, 626) in dry ethanol (100 ml) at 70° C. under nitrogen. The mixture was cooled to room temperature and iodoacetonitrile (355 μl) was added. After stirring for 15 min the solvent was removed in vacuo. The residue was partitioned between ethyl acetate (50 ml) and water (50 ml). The organic phase was extracted with 2×50 ml of water and dried over sodium sulfate. Removal of the solvent gave the pure title compound as white crystals. Yield 1.06 g (91%), mp 130.5–131.5° C., $^1$H-NMR (DMSO-d$_6$), δ (ppm): 9.48 (s, 1H, NH), 7.23 (d, J=9 Hz, 1H), 7.08 (d, J=3 Hz, 1H), 6.88 (dd, 1H), 4.18 (s, 2H, CH$_2$), 3.78 (s, 3H, CH$_3$O), 2.01 (s, 3H, CH$_3$).

b) N-(2-Cyanomethylsulfonyl-4-methoxyphenyl)acetamide

Oxidation of N-(2-cyanomethylsulfanyl-4-methoxyphenyl)acetamide (0.95 g) with hydrogen peroxide in glacial acetic acid by a procedure similar to the procedure described in EXAMPLE 2 gave the title compound as pale yellow crystals. Yield 0.59 g, $^1$H-NMR (DMSO-d$_6$), δ (ppm): 9.54 (br s, 1H, NH), 7.70–7.62 (m, 1H, Ar—H), 7.46–7.35 (m, 2H, Ar—H), 5.20 (s, 2H, CH$_2$), 3.84 (s, 3H, CH$_3$O), 2.07 (s, 3H, CH$_3$).

c) 3-Methyl-7-methoxy-4H-1,4-benzothiazine-2-carbonitrile 1,1-dioxide

Treatment of N-(2-cyanomethylsulfonyl-4-methoxyphenyl)acetamide with aqueous sodium hydroxide by a procedure similar to the procedure described in EXAMPLE 1 c) gave the title compound; mp 307–308° C. (from methanol), $^1$H-NMR (DMSO-d$_6$), δ (ppm): 11.89 (br s, 1H, NH), 7.51–7.27 (m, 3H, Ar—H), 3.86 (s, 3H, CH$_3$O), 2.44 (s, 3H, CH$_3$).

Example 11

6-Fluoro-3-methyl-4H-1,4-benzothiazine-2-carbonitrile 1,1-dioxide a) (2-Amino-4-fluoro-phenylsulfanyl)acetonitrile A suspension of 2-amino-5-fluoro-benzothiazole (3.45 g) was stirred for 7 h at 165–170 °C. under nitrogen in a solution of potassium hydroxide (6.9 g) in water (13.5 ml). The resulting mixture was cooled on an ice bath to 10° C., supplemented with water (5 ml) and then a solution of acetic acid (3.5 ml) in water (4 ml). The mixture was diluted with 96% ethanol (20 ml) and subsequently a solution of iodoacetonitrile (3.42 g) in 96% ethanol (5 ml) was added. After stirring for 15 min the mixture was adjusted to pH ~7 by adding acetic acid and approx. half of the solvent was removed in vacuo. The residue was diluted with water (100 ml) and extracted with ethyl acetate (50+3×25 ml). The combined extracts were dried over sodium sulfate, filtered and evaporated to give the title compound as a practically pure yellow oil. Yield 3.60 g (96%); $^1$H-NMR (DMSO-d$_6$), δ (ppm): 7.32–7.43 (dd, 1H, Ar—H), 6.49–6.60 (dd, 1H, Ar—H), 6.29–6.43 (ddd, 1H, Ar—H), 5.88 (br, 2H, NH$_2$), 3.82 (s, 2H, CH$_2$).

b) N-(2-Cyanomethylsulfanyl-5-fluoro-phenyl)acetamid

Acetyl chloride (1.5 ml) in THF (10 ml) and subsequently pyridine (1.7 ml) in THF (10 ml) was added to a stirred solution of (2-amino-4-fluoro-phenylsulfanyl)acetonitrile (3.5 g) in THF (30 ml) at 0° C. The mixture was stirred at 0° C. for 50 min. Then the solvent was removed in vacuo and the residue was triturated with water (80 ml). The precipitate was filtered off and dried yielding 3.7 g (86%) of the title compound as yellow crystals; mp 113–115° C.; $^1$H-NMR (DMSO-$d_6$), δ (ppm): 9.59 (s, 1H, NH), 7.73–7.57 (m, 2H, Ar—H), 7.19–7.05 (m, 1H, Ar—H), 4.05 (s, 2H, $CH_2$), 2.12 (s, 3H, $CH_3$). The title compound was used for the next step without further purification.

c) N-(2-Cyanomethylsulfonyl-5-fluoro-phenyl)acetamide

N-(2-Cyanomethylsulfanyl-5-fluoro-phenyl)acetamide was oxidized by a procedure similar to the one described in EXAMPLE 2 d) to give the title compound as white crystals, mp 131–132° C.; $^1$H-NMR (DMSO-$d_6$), δ (ppm): 9.65 (s, 1H, NH), 8.07–7.93 (m, 2H, Ar—H), 7.41–7.28 (m, 1H, Ar—H), 5.32 (s, 2H, $CH_2$), 2.16 (s, 3H, $CH_3$).

d) 6-Fluoro-3-methyl-4H-1,4-benzothiazine-2-carbonitrile 1,1-dioxide

Treatment of N-(2-cyanomethylsulfonyl-5-fluoro-phenyl) acetamide with aqueous sodium hydroxide by a procedure similar to the procedure described in EXAMPLE 1 c) gave the title compound; mp 261–263° C. (sinters at 240–251° C.), $^1$H-NMR (DMSO-$d_6$), δ (ppm): 12.03 (br s, 1H, NH), 8.06 (dd, 9.0 Hz/5.5 Hz, 1H, H8), 7.35 (m, 1H, H7), 7.20 (dd, 10.0/2.5 Hz, 1H, H5), 2.46 (s, 3H, $CH_3$).

What is claimed is:

1. A compound of the general formula I:

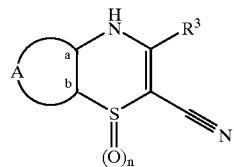

(I)

wherein n is 1 or 2;

$R^3$ is $C_{1-6}$-alkyl, $C_{2-6}$-alkenyl, $C_{2-6}$-alkynyl, $C_{3-6}$-cycloalkyl, $C_{3-6}$-cycloalkyl-$C_{1-6}$-alkyl or $C_{1-6}$-alkyl-$C_{3-6}$-cycloalkyl, optionally being mono- or polysubstituted with hydroxy or halogen;

A together with the carbon atoms a and b of formula (I) is

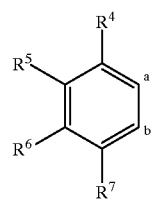

wherein $R^4$, $R^5$, $R^6$, $R^7$ independently are hydrogen; halogen; hydroxy; cyano; trifluoromethyl; trifluoromethylsulfanyl; trifluoromethoxy; $C_{1-6}$-alkyl; $C_{1-6}$-alkoxy; $C_{1-6}$-alkoxy-$C_{1-6}$-alkyl; $C_{1-6}$-alkylsulfanyl; $C_{1-6}$-alkylsulfonyl; $C_{1-6}$-alkylsulfinyl;

or a salt thereof with a pharmaceutically acceptable acid or base.

2. A compound according to claim 1 wherein n is 2.

3. A compound according to claim 1 wherein $R^3$ is $C_{1-6}$-alkyl.

4. A compound according to claim 3 wherein $R^3$ is methyl.

5. A compound according to claim 1 wherein $R^4$, $R^5$, $R^6$, $R^7$ independently are hydrogen, halogen, trifluoromethyl, trifluoromethoxy or trifluoromethylsulfanyl.

6. A compound according to claim 1 wherein $R^4$ is hydrogen and $R^5$, $R^6$, $R^7$ independently are hydrogen, halogen, trifluoromethyl, trifluoromethoxy or trifluoromethylsulfanyl.

7. A compound according to claim 1 wherein $R^5$ and $R^6$ independently are trifluoromethyl or halogen, and $R^4$ and $R^7$ are hydrogen.

8. A compound according to claim 1 wherein $R^4$, $R^6$ and $R^7$ are hydrogen, and $R^5$ is halogen, trifluoromethyl, trifluoromethoxy or trifluoromethylsulfanyl.

9. A compound according to claim 1 wherein $R^4$, $R^5$ and $R^7$ are hydrogen, and $R^6$ is halogen, trifluoromethyl, trifluoromethoxy or trifluoromethylsulfanyl.

10. A compound according to claim 1 selected from the following:

7-Chloro-3-methyl-4H-1,4-benzothiazine-2-carbonitrile 1,1-dioxide;

3-Methyl-6-trifluoromethyl-4H-1,4-benzothiazine-2-carbonitrile 1,1-dioxide;

3-Methyl-6-trifluoromethyl-4H-1,4-benzothiazine-2-carbonitrile 1-oxide;

7-Chloro-3-propyl-4H-1,4-benzothiazine-2-carbonitrile 1,1-dioxide;

7-Chloro-3-isopropyl-4H-1,4-benzothiazine-2-carbonitrile 1,1-dioxide;

3-tert-Butyl-7-chloro-4H-1,4-benzothiazine-2-carbonitrile 1,1-dioxide;

7-Methoxy-3-methyl-4H-1,4-benzothiazine-2-carbonitrile 1,1-dioxide;

7-Methoxy-3-propyl-4H-1,4-benzothiazine-2-carbonitrile 1,1-dioxide;

7-Methoxy-3-isopropyl-4H-1,4-benzothiazine-2-carbonitrile 1,1-dioxide;

3-tert-Butyl-7-methoxy-4H-1,4-benzothiazine-2-carbonitrile 1,1-dioxide;

6,7-Dichloro-3-methyl-4H-1,4-benzothiazine-2-carbonitrile 1,1-dioxide;

6-Fluoro-3-methyl-4H-1,4-benzothiazine-2-carbonitrile 1,1-dioxide;

6-Chloro-3-methyl-4H-1,4-benzothiazine-2-carbonitrile 1,1-dioxide;

8-Fluoro-3-methyl-6-trifluoromethyl-4H-1,4-benzothiazine-2-carbonitrile 1,1-dioxide;

6-Chloro-3-methyl-4H-thieno[2,3-b]-1,4-thiazine-2-carbonitrile 1,1-dioxide;

or a salt thereof with a pharmaceutically acceptable acid or base.

11. A compound according to claim 1 selected from the following:

3-Propyl-6-trifluoromethyl-4H-1,4-benzothiazine-2-carbonitrile 1,1-dioxide;

5,7-Difluoro-3-methyl-4H-1,4-benzothiazine-2-carbonitrile 1,1-dioxide;

7-Fluoro-3-methyl-4H-1,4-benzothiazine-2-carbonitrile 1,1-dioxide;

6-Chloro-7-fluoro-3-methyl-4H-1,4-benzothiazine-2-carbonitrile 1,1-dioxide;

3-Methyl-7-trifluoromethylsultanyl-4H-1,4-benzothiazine-2-carbonitrile 1,1-dioxide;

3-Methyl-7-trifluoromethoxy-4H-1,4-benzothiazine-2-carbonitrile 1,1-dioxide;

6,7,8-Trichloro-3-methyl-4H-1,4-benzothiazine-2-carbonitrile 1,1-dioxide;

or a salt thereof with a pharmaceutically acceptable acid or base.

12. A pharmaceutical composition comprising a compound according to claim 1 or a pharmaceutical acceptable salt thereof with a pharmaceutically acceptable acid or base, or any optical isomer or mixture of optical isomers, including a racemic mixture, or any tautomeric form together with one or more pharmaceutically acceptable carriers or diluents.

13. The pharmaceutical composition according to claim 12 in the form of an oral dosage unit or parenteral dosage unit.

14. A pharmaceutical composition according to claim 12 wherein said compound is administered as a dose in a range from about 0.05 to 1000, preferably from about 0.1 to 500 and especially in the range from 50 to 200 mg per day.

15. A method of treating hyperinsulinaemia in a subject in need thereof comprising administering an effective amount of a compound according to claim 1 to said subject.

16. A method of treating non-insulin dependent diabetes mellitus (NIDDM) in a subject in need thereof comprising administering an effective amount of a compound according to claim 1 to said subject.

17. A method of treating impaired fasting glucose (IFG) or impaired glucose tolerance (IGT) in a subject in need thereof comprising administering an effective amount of a compound according to claim 1 to said subject.

18. A method of treating insulin dependent diabetes (IDDM) in a subject in need thereof comprising administering an effective amount of a compound according to claim 1 to said subject.

* * * * *